US007422110B2

(12) United States Patent
Zanden et al.

(10) Patent No.: US 7,422,110 B2
(45) **Date of Patent: *Sep. 9, 2008**

(54) TITRATION/COMPLIANCE PACK WITH INCREASING DOSES

(75) Inventors: John Jacob Vander Zanden, Dana Point, CA (US); Rodney Terwilliger, Buena Park, CA (US)

(73) Assignee: Allergan, Inc., Irvine, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/438,027

(22) Filed: May 19, 2006

(65) Prior Publication Data

US 2006/0231452 A1 Oct. 19, 2006

Related U.S. Application Data

(63) Continuation of application No. 10/622,170, filed on Jul. 16, 2003, now Pat. No. 7,086,532.

(51) Int. Cl.
*B65D 83/04* (2006.01)
*A61K 9/00* (2006.01)
*A61K 31/13* (2006.01)

(52) U.S. Cl. ....................... 206/534; 206/531; 206/532; 206/539; 424/400; 514/662

(58) Field of Classification Search ................. 206/528, 206/531-532, 534-534.2, 538-539; 424/400; 514/662
See application file for complete search history.

(56) References Cited

U.S. PATENT DOCUMENTS 2,415,859 A 1/1947 Ancker
3,099,352 A 7/1963 Aven
3,225,913 A 12/1965 Lee
3,568,828 A 3/1971 Lerner
3,738,480 A 6/1973 Chesley
3,826,222 A 7/1974 Romick
3,921,806 A 11/1975 Wawracz
RE29,705 E 7/1978 Compere
4,148,273 A 4/1979 Hollingsworth et al.
4,473,156 A 9/1984 Martin
4,473,884 A 9/1984 Behl
4,617,557 A 10/1986 Gordon
4,706,815 A 11/1987 Curtis et al.
4,883,180 A 11/1989 Humphrey et al.
4,958,736 A 9/1990 Urheim (Continued)

FOREIGN PATENT DOCUMENTS

CA 2218470 12/1997

(Continued)

*Primary Examiner*—Bryon P Gehman
(74) *Attorney, Agent, or Firm*—Allergan, Inc.; Martin Voet; Brent A. Johnson

(57) ABSTRACT

A titration package and method for enabling compliance with a regime of changing dosage of medication over a period of time includes a backing having an array of receivers with the array including a plurality of columns and a plurality of rows. A plurality of sets of tablets are provided with each tablet in set having a common dose of medication and a different dose than a tablet of a different set. Each set of tablets is disposed in receivers of one having an adjacent row and an adjacent column. Indicia is provided and disposed adjacent to the columns and rows for displaying common days and successive weeks.

11 Claims, 2 Drawing Sheets

100

| | WEEK 1 | WEEK 2 | WEEK 3 | WEEK 4 | WEEK 5 | WEEK 6 | WEEK 7 | WEEK 8 |
|---|---|---|---|---|---|---|---|---|
| SUN | 5 | 5 | 10 | 10 | 15 | 15 | 20 | 20 |
| MON | 5 | 5 | 10 | 10 | 15 | 15 | 20 | 20 |
| TUE | 5 | 5 | 10 | 10 | 15 | 15 | 20 | 20 |
| WED | 5 | 5 | 10 | 10 | 15 | 15 | 20 | 20 |
| THU | 5 | 5 | 10 | 10 | 15 | 15 | 20 | 20 |
| FRI | 5 | 5 | 10 | 10 | 15 | 15 | 20 | 20 |
| SAT | 5 | 5 | 10 | 10 | 15 | 15 | 20 | 20 |

U.S. PATENT DOCUMENTS

| | | | | |
|---|---|---|---|---|
| D330,331 | S | 10/1992 | Hsiao | |
| 5,288,107 | A | 2/1994 | Johnson et al. | |
| D383,668 | S | 9/1997 | Siegel | |
| 5,747,545 | A | 5/1998 | Lipton | |
| 5,752,235 | A | 5/1998 | Kehr et al. | |
| 5,922,773 | A | 7/1999 | Lipton et al. | |
| 6,047,829 | A | 4/2000 | Johnstone et al. | |
| 6,169,707 | B1 | 1/2001 | Newland | |
| 6,375,956 | B1 | 4/2002 | Hermelin et al. | |
| 6,411,567 | B1 | 6/2002 | Niemiec et al. | |
| 6,471,645 | B1 | 10/2002 | Warkentin et al. | |
| 6,491,211 | B1 | 12/2002 | Evans et al. | |
| 6,564,945 | B1 | 5/2003 | Weinstein et al. | |
| 6,651,816 | B2 | 11/2003 | Weinstein | |
| 7,086,532 | B2 * | 8/2006 | Zanden et al. | 206/534 |
| 2004/0176381 | A1 | 9/2004 | Wash | |

FOREIGN PATENT DOCUMENTS

| | | | |
|---|---|---|---|
| EP | 0852208 | A1 | 6/1996 |
| WO | WO97/03896 | | 2/1997 |
| WO | WO03/032891 | A1 | 10/2002 |

* cited by examiner

TITRATION/COMPLIANCE PACK WITH INCREASING DOSES

The present application is a continuation of U.S. Ser. No. 10/622,170 filed Jul. 16, 2003, now U.S. Pat. No. 7,086,532.

The present invention is generally directed to a titration package for enabling compliance with a regimen of changing dosage of medication over a period of time and is more particularly directed to a dosage pack for dosing of oral Memantine for the indication of preventing further nerve cell loss in glaucoma patients.

Glaucoma is characterized by damaged to the optic nerve which is typically accompanied by a decrease in normal vision field. An early sign of possible glaucomatous visual field loss is elevated interocular pressure.

In that regard, glaucoma has typically been treated by medically and/or surgically lowering elevated interocular pressure. Memantine and other compounds suitable for chronic administration should be administered to avoid adverse events associated with the drug, for example, patients prescribed Memantine therapy need to be titrated upwards from 5 mg of Memantine per day to a maintenance dose of either 10 mg or 20 mg per day. Memantine approved for other indications also requires similar titration schedules to avoid drug-related adverse events.

The present invention is directed to a titration package for enabling compliance with a regimen of changing dosage of medication over a period of time and further provides for a method of treating a human patient to reduce damage to retinal ganglion cells associated with glaucoma utilizing the titration package in accordance with the present invention.

SUMMARY OF THE INVENTION

A titration package for enabling compliance with a regimen of changing dosage of medication over a period of time in accordance with the present invention generally includes a backing having an array of receivers with the array including a plurality of columns and a plurality of rows.

A plurality of sets of tablets are provided in the receivers. Each tablet in a set has a common dose of medication and a different dose than a tablet of a different set. Each set of tablets is disposed in receivers of one of an adjacent row and an adjacent column.

Indicia is provided and disposed adjacent the columns and rows for displaying common days and successive weeks. Thus, the package provides for a titration schedule which prevents adverse events as a result of mis-dosing. As a result, the package in accordance with the present invention provides for a safer and accordingly more beneficial method for enabling compliance with the regimen.

More particularly, in one embodiment of the present invention different sets of tablets are disposed in different rows with each row being indicated by a successive week and each column being indicated as a different day of the week. In this embodiment, the sets of tablets having increased doses are disposed in receivers in rows indicated as successive weeks. More specifically, the sets of tablets have 5 mg, 10 mg, 15 mg and 20 mg doses of Memantine.

In an alternative embodiment, different sets of tablets are disposed in different columns, with each column being indicated as a successive week and each row being indicated as a different day of the week.

In yet another embodiment of the present invention, the titration package for enabling compliance with a regimen of changing doses of medication over a period of time includes a backing having an array or receivers with the array including a plurality of columns and a plurality of rows. In this embodiment, a plurality of sets of tablets are provided with each set being disposed in receivers of a plurality of adjacent rows or a plurality of adjacent columns. This plurality may be two and each tablet in a set has a common dose of medication and a different dose than a tablet in a different set.

Preferably, in this embodiment pairs of adjacent rows have differing sets of tablets. This enables the change of dosage over an eight-week period of time from 5 mg to 20 mg doses of Memantine.

Thus, the present invention provides for a method for enabling compliance with a regimen of changing dosage of medication with the method comprising the steps of providing a backing having an array of receivers, with the array including a plurality of columns and a plurality of rows. The method further includes disposing a plurality of sets of tablets and the receivers with each tablet in the set having a common dose of medication and a different dose than a tablet of a different set. Each set is disposed in receivers of one of an adjacent row and an adjacent column. The method finally includes a step of providing indicia adjacent the columns and rows indicating common days and successive weeks.

A concomitant method in accordance with the present invention provides for a method of treating a human patient to reduce damage to retinal ganglion cells associated with glaucoma with the method comprising providing a titration package for enabling compliance with a regimen of changing dosage of medication over a period of time. The package includes the elements hereinabove recited and further the medication comprises Memantine.

BRIEF DESCRIPTION OF THE DRAWINGS

The present invention may be more clearly understood with reference to the following detailed description in conjunction with the appended drawings of which.

DETAILED DESCRIPTION

The titration package and method in accordance to the present invention is particularly useful for the dosage of oral medication for infirmed and elderly patients and accordingly the manipulation of tablets enabled by the present invention and tracking of compliance with a titration schedule is a great advantage. In the case of treatment of glaucoma, and the use of a medicament, such as, for example Memantine, the progression of blindness also demands a need for the present invention.

Figure 1:
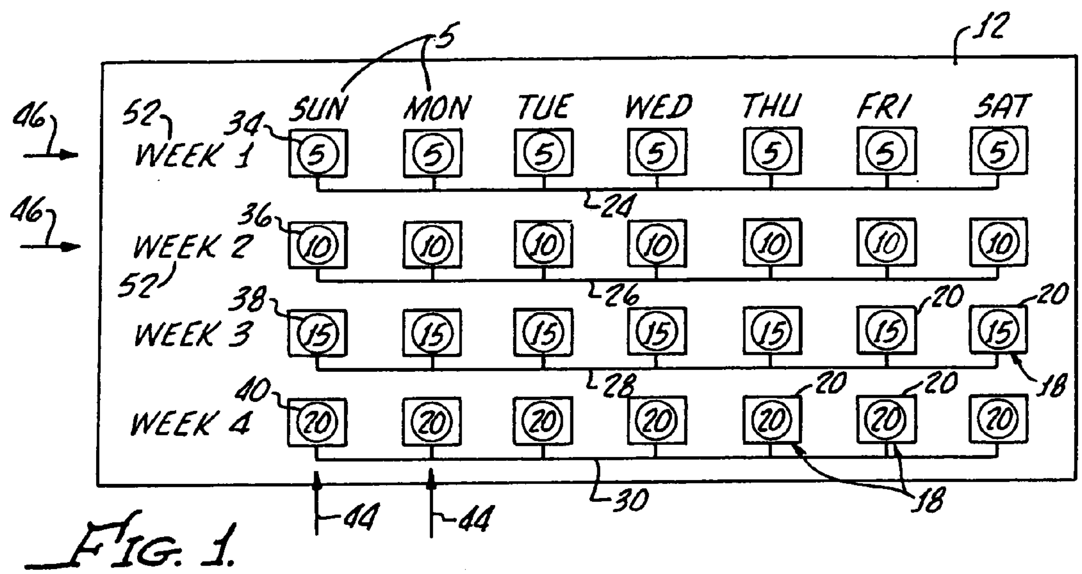
FIG. 1 is a representation of a titration package in accordance with the present invention for enabling compliance with a regimen of changing dosage of medication over a four-week period of time.

With reference to FIG. 1, there is represented a titration package 10 for enabling compliance with a regimen of changing dosage of medication over a period of time, for example four weeks with the package 10 including a backing 12 which includes an array 18 of receivers holding a plurality of sets 24, 26, 28, 30 of tablets 34, 36, 38, 40.

The receivers 20 may be conventional, rupturable blisters as, for example, as set forth in U.S. Pat. No. RE 29,705 which is to be incorporated herewith in its entirety for the purpose of describing the type of rupturable receivers suitable for use with the present invention.

The backing 12 may be any suitable plastic or paperboard backing and may be incorporated into protective coverings, not shown, such as, for example, shown in U.S. Pat. No. 6,047,829. This patent is to also be incorporated herewith in its entirety by this specific reference thereto for showing a backing and dispensing package construction suitable for use in the present invention.

With continued reference to FIG. 1, the array 18 of receivers 20 includes a plurality of columns indicated by the arrows 44 and a plurality of rows indicated by the arrows 46. Indicia 50, 52 is provided and disposed adjacent the columns 44 and rows 46, preferably on the backing 12 displays common days and successive weeks.

As shown in FIG. 1, different sets are disposed in different rows 46 as indicated by week 1, week 2, week 3, and week 4. The number following the indicia "week" indicating successive weeks and the columns 44 indicated as Sunday, Monday, Tuesday, Wednesday, Thursday, Friday, and Saturday indicating different days of the week.

With regard to the treatment of glaucoma, the set 24 includes 5 mg of Memantine, the set 26 includes tablets of 10 mg of Memantine, the set 28 includes tablets of 15 mg of Memantine, and the set 30 includes tablets of 20 mg of Memantine arranged in the rows 46 indicated as week 1, week 2, week 3, and week 4. In accordance with the present invention, a patient utilizing the package and method of the present invention is titrated from a 5 mg dose to a 20 mg dose of the Memantine.

In use, a patient beginning the regimen may start on any given day of the week, for example, Tuesday and progressively take the tablets by rupturing the receivers 20 along a row until all of the tablets 34 have been dispensed. At that time, the patient begins week 2 of the regimen by taking the tablets 36 disposed in the row 46 indicated by the indicia, week 2.

Thus, the arrangement and dosages of the tablets therein enables compliance with the regimen of changing the dosage of the medication over the period of time, four weeks as indicated in FIG. 1.

Figure 2:
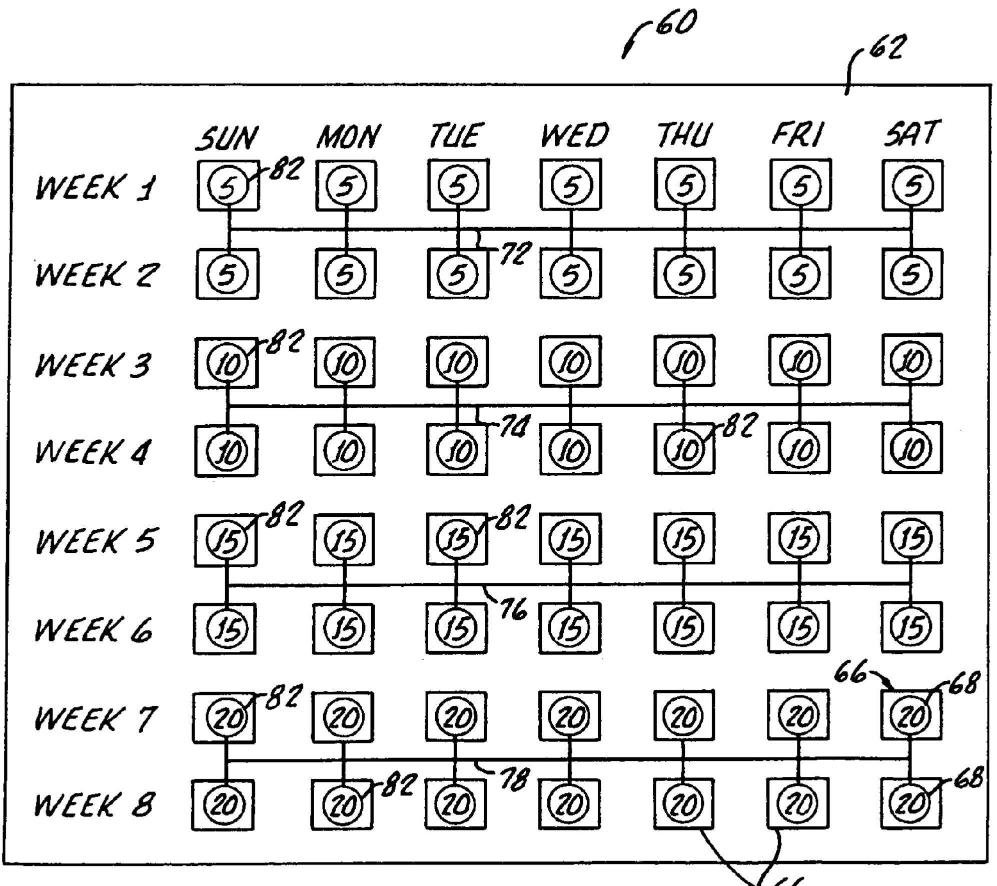
FIG. 2 is a representation of a titration package similar to that shown in FIG. 1 enabling compliance with a regimen of changing dosage of medication over a period of eight weeks.

With reference to FIG. 2, there is shown an alternative embodiment, or package, 60 in accordance with the present invention for enabling compliance with a regimen of changing dosage of medication over a period of 8 weeks. In this embodiment, a backing 62 is provided with an array 66 of receivers 68 with the array being arranged in rows indicated by the indicia, "week 1-8" and columns indicated as "Sun-Sat".

Figure 3:
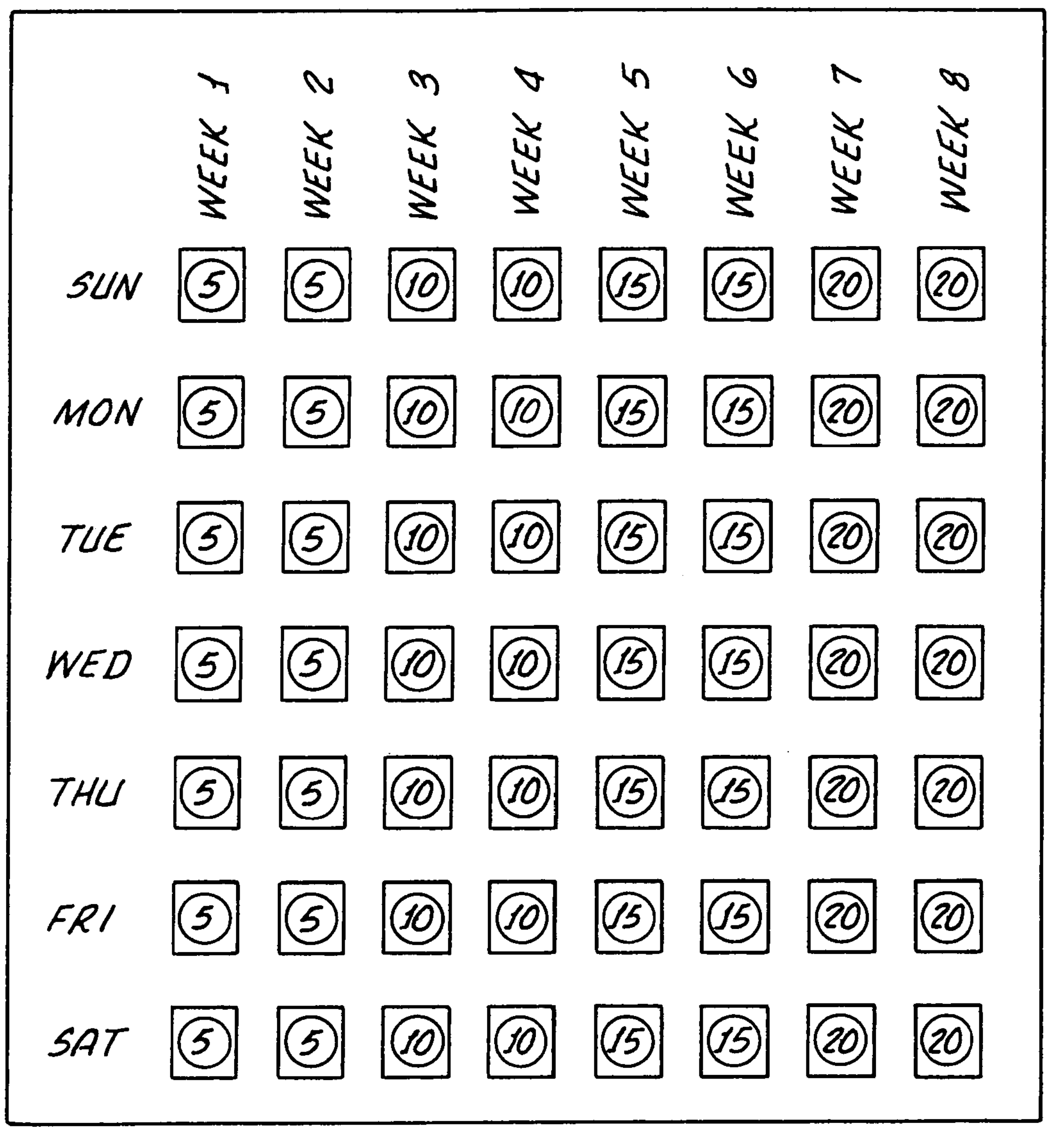
FIG. 3 is a representation similar to the titration package shown in FIG. 2 showing an alternative arrangement of days and successive weeks, as will be hereinafter described.

In this embodiment, different sets 72, 74, 76, 78 of tablets 82 are disposed in adjacent rows as shown in FIG. 2 or an adjacent columns as shown in the embodiment 100 of FIG. 3. Character references have been omitted from FIG. 3 to reduce redundancy in description. It should be clear that the embodiment of 60 and 100 are identical except for the arrangement of columns and rows.

In a method of treating a human patient in accordance with the present invention to reduce damage to retinal ganglion cells associated with glaucoma, the titration packages 60, 100 enable compliance with a regimen of changing dosage of medication over a period of time as hereinabove described in connection with the package 10 shown in FIG. 1.

The patient beginning on any of the week completes the removal and use of tablets in a corresponding week in adjacent rows or column before proceeding to the next pair of adjacent rows or columns in a manner as described hereinabove in connection with the embodiment 10 shown in FIG. 1.

Although there has been hereinabove described a specific titration/compliance pack in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclose herein. Accordingly, any and all modifications, variations or equivalent arrangements which may occur to those skilled in the art, should be considered to be within the scope of the present invention as defined in the appended claims.

What is claimed is:

1. A titration package for enabling compliance with a regimen of changing dosage of medication over a period of time, the package comprising:

a backing having an array of receivers, said array including a plurality of columns and a plurality of rows;

a plurality of sets of Memantine tablets, each tablet in a set having a common dose of Memantine and a different dose than a Memantine tablet of a different set, each set being disposed in receivers of one of an adjacent row and an adjacent column; different sets of Memantine tablets are disposed in different rows, each row being indicated as a successive week, each column being indicated as a different day of the week, sets of Memantine tablets having increased doses being disposed in receivers of rows indicated as successive weeks; and indicia disposed adjacent the columns and rows for displaying common days and successive weeks.

2. The package according to claim 1 wherein the sets of tablets have 5 mg, 10 mg, 15 mg, and 20 mg doses of Memantine.

3. A titration package for enabling compliance with a regimen of changing dosage of medication over a period of time, the package comprising:

a backing having an array of receivers, said array including a plurality of columns and a plurality of rows;

a plurality of sets of tablets, each tablet in a set having a common dose of the medication and a different dose than a tablet of a different set, each set being disposed in receivers of one of an adjacent row and an adjacent column; different sets of tablets are disposed in a different plurality of columns, each plurality of columns being indicated as a successive week, each row being indicated as a different day of the week, sets of tablets having increased doses being disposed in receivers of a plurality of columns indicated as successive weeks; and indicia disposed adjacent the columns and rows for displaying common days and successive weeks.

4. The package according to claim 3 wherein the sets of tablets have 5 mg, 10 mg, 15 mg, and 20 mg doses of Memantine.

5. A titration package for enabling compliance with a regimen of changing dosage of medication over a period of time, the package comprising:

a backing having an array of receivers, said array including a plurality of columns and a plurality of rows;

a plurality of sets of tablets, each tablet in a set having a common dose of the medication and a different dose than a tablet of a different set, each set being disposed in receivers of a plurality of adjacent rows, different sets of tablets are disposed in a different plurality of rows, each plurality of rows being indicated as a successive week, each column being indicated as a different day of the week, sets of tables having increased doses being disposed in receivers of a plurality of rows indicated as successive weeks; and indicia disposed adjacent the columns and rows for displaying common days and successive weeks.

6. The package according to claim 5 wherein pairs of adjacent rows have differing sets of tablets.

7. The package according to claim 5 wherein the sets of tablets have 5 mg, 10 mg, 15 mg, and 20 mg doses of Memantine.

8. The package according to claim 5 wherein pairs of adjacent columns have differing sets of tablets.

9. The package according to claim 8 wherein each pair of columns is indicated as a successive week and each row is indicated as a different day of the week.

10. The package according to claim 9 wherein sets of tablets having increased doses are disposed in receivers of adjacent pairs of columns.

11. The package according to claim 10 wherein the sets of tablets have 5 mg, 10 mg, 15 mg, and 20 mg doses of Memantine.

* * * * *